United States Patent [19]

Francischelli et al.

[11] Patent Number: 5,607,385
[45] Date of Patent: Mar. 4, 1997

[54] DEVICE AND ALGORITHM FOR A COMBINED CARDIOMYOSTIMULATOR AND A CARDIAC PACER-CARIOVERTER-DEFIBRILLATOR

[75] Inventors: David Francischelli, Anoka; Kendra K. Gealow, Plymouth, both of Minn.; Pierre A. Grandjean, Warsage, Belgium; John Hammargren, Medina, Minn.; Johann J. Neisz, Coon Rapids, Minn.; David K. Peterson, Moundsview, Minn.

[73] Assignee: Medtronic, Inc., Minneapolis, Minn.

[21] Appl. No.: 516,081

[22] Filed: Aug. 17, 1995

[51] Int. Cl.$^6$ ..................................................... A61N 1/368
[52] U.S. Cl. .............................................. 600/17; 607/4
[58] Field of Search ............................... 607/4, 17, 25, 607/48; 600/17, 16; 128/702, 703, 705

[56] References Cited

U.S. PATENT DOCUMENTS

| | | | |
|---|---|---|---|
| 4,830,006 | 5/1989 | Haluska et al. | 607/4 |
| 4,971,058 | 11/1990 | Pless et al. | 607/4 |
| 5,086,772 | 2/1992 | Larnard et al. | 607/4 |
| 5,251,621 | 10/1993 | Collins | 607/4 |
| 5,458,619 | 10/1995 | Olson | 607/4 |

Primary Examiner—William E. Kamm
Assistant Examiner—George R. Evanisko
Attorney, Agent, or Firm—Michael J. Jaro; Harold R. Patton

[57] ABSTRACT

A device and algorithm for a combined cardiomyostimulator and a cardiac pacer-cardioverter-defibrillator. In particular the present device operates, in a first embodiment, to deliver stimulation to a skeletal muscle grafted about a heart; sense depolarizations of a patient's heart; measure the intervals separating successive depolarizations of the patient's heart; define first and second interval ranges; determine the number of the measured intervals falling within the first and second interval ranges; inhibit the delivery of stimulation to a skeletal muscle grafted about a heart upon the sensing of a depolarization within the first or second interval range; detect the occurrence of a first type of arrhythmia when the number of the measured intervals falling within the first interval range equals a first predetermined value; detect the occurrence of a second type of an arrhythmia when the number of the intervals falling within the second interval range equals a second predetermined value; deliver a first type of arrhythmia therapy in response to the detection of the first arrhythmia; and deliver a second type of arrhythmia therapy in response to the detection of the second arrhythmia, the second type of arrhythmia therapy having a cardiac stimulation component and a skeletal muscle component.

8 Claims, 7 Drawing Sheets 5,607,385

DEVICE AND ALGORITHM FOR A COMBINED CARDIOMYOSTIMULATOR AND A CARDIAC PACER-CARIOVERTER-DEFIBRILLATOR

FIELD OF THE INVENTION

The present invention generally relates to cardiac assist systems, including cardiomyoplasty, for the treatment of patients needing augmented cardiac output. More specifically, the present invention relates to a device and algorithm for a combined cardiomyostimulator and cardiac pacer-cardioverter-defibrillator.

BACKGROUND OF THE INVENTION

Cardiac assist systems aid patients with chronically and unacceptably low cardiac output who cannot have their cardiac output raised to acceptable levels by traditional treatments, such as drug therapy. One particular type of cardiac assist system currently used is a cardiomyoplasty.

Essentially a cardiomyoplasty provides a muscle-powered cardiac assist system. As seen in U.S. Pat. No. 4,813,952 of Khalafalla, incorporated herein by reference, the cardiomyoplasty is a cardiac assist system powered by a surgically-modified muscle tissue, such as the latissimus dorsi. In particular, the latissimus dorsi is wrapped around the heart. An implantable pulse generator is provided. The implantable pulse generator senses contractions of the heart via one or more sensing leads and stimulates the appropriate nerves of the muscle tissue with burst signals to cause the muscle tissue to contract in synchrony with the heart. As a result, the heart is assisted in its contractions, thereby raising the stroke volume and thus cardiac output. Besides delivering therapeutic electrical pulses to the muscle, the pulse generator is quite often also coupled so as to also provide therapeutic electrical pulses to the heart. See, for example, U.S. Pat. No. 4,735,205 of Chachques et al., incorporated herein by reference.

Patients with chronic cardiac output deficiencies, although treatable through cardiomyoplasty, face an increased risk for cardiac arrhythmic episodes, such as ventricular tachycardia or fibrillation. These arrhythmic episodes may be life-threatening.

In order to treat these potentially life-threatening cardiac arrhythmias, some cardiac assist systems have been proposed which combine a muscle stimulator as well as a cardiac pacer-cardioverter-defibrillator. In such a manner a patient who has had a cardiomyoplasty may, in addition to receiving musclepowered cardiac assistance, also receive various types of therapeutic cardiac electrical stimulation. One example of such a system may be seen in the U.S. Pat. No. 5,251,621 issued to Collins and entitled "Arrhythmia Control Pacer Using Skeletal Muscle Cardiac Graft Stimulation."

One problem associated with devices which combine a muscle stimulator as well as a cardiac pacer-cardioverter-defibrillator is that the muscle stimulation may interfere with the reliable sensing of cardiac events. During ventricular arrhythmias, such as ventricular fibrillation or ventricular tachycardia (hereafter "VF" and "VT" respectively) the cardiac signals may have very low amplitudes. This is especially the case during VF. The stimulation of the muscle wrap at that time could thus interfere with reliably sensing the VF or VT due to post-pace polarization, cross talk, et cetera.

The U.S. Pat. No. 5,251,621 issued to Collins offers one solution to this problem. The Collins patent discloses a cross channel blanking control signal to disable pacemaker sensing during generation of a skeletal muscle stimulation pulse. This is intended to prevent the pacemaker from incorrectly classifying a skeletal muscle stimulation pulse as an episode of intrinsic cardiac activity. At all times, however, muscle stimulation is continued. In fact, during arrhythmic events besides muscle stimulation continuing, Collins discloses adjusting various parameter of the muscle stimulation bursts, such as pulse amplitude, duration as well as the interval between pulses within a burst. One problem with this approach, however, is the continuation of skeletal muscle stimulation may interfere with the reliable sensing of the arrhythmia. Moreover, adjusting the various parameters of the muscle stimulation signal, such as amplitude or duration, creates an even greater likelihood that the device will not be able to reliably sense the arrhythmia.

Rapid detection of a cardiac tachyarrhythmia, and especially VF, is very important. A typical cardiac pacer-cardioverter-defibrillator detection algorithm requires the detection of a certain number of tachyarrhythmic events within a specified time period. In the case of VF detection, these devices will typically initiate the charging of a cardiac output circuit. This charging period may last between 1 to 21 seconds, depending on the therapy to be delivered. Following charging, the detection algorithm would once again confirm VF and deliver the therapy. Once the therapy was delivered, the detection algorithm would remain active until the tachyarrhythmic episode termination was confirmed.

At high energy levels, the period from tachyarrhythmia detection until tachyarrhythmia termination confirmation and muscle therapy reactivation could be extremely long, up to 35 seconds, or even longer. The consequence of this inhibition of the cardiac assistance during an episode of tachyarrhythmia is that cardiac output is highly compromised. In addition, while in fibrillation the threshold to achieve defibrillation through electrical shock rises exponentially. Higher defibrillation thresholds, however, mean the device must feature larger capacitors or higher voltages or both.

SUMMARY OF THE INVENTION

It is thus an object of the invention to provide a cardiac assist system which permits the rapid detection of a cardiac arrhythmia.

It is a further object of the present invention to provide a cardiac assist system which provides cardiac assistance during a cardiac arrhythmia.

These and other objects are met by the present invention which comprises a device and algorithm for a combined cardiomyostimulator and a cardiac pacer-cardioverter-defibrillator. In particular the present invention operates, in a first embodiment, to deliver stimulation to a skeletal muscle grafted about a heart; sense depolarizations of a patient's heart; measure the intervals separating successive depolarizations of the patient's heart; define first and second interval ranges; determine the number of the measured intervals falling within the first and second interval ranges; inhibit the delivery of stimulation to a skeletal muscle grafted about a heart upon the sensing of a depolarization within the first or second interval range; detect the occurrence of a first type of arrhythmia when the number of the measured intervals falling within the first interval range equals a first predetermined value; detect the occurrence of a second type of an arrhythmia when the number of the intervals falling within the second interval range equals a second predetermined value; deliver a first type of arrhythmia therapy in response to the detection of the first arrhythmia; and deliver a second type of arrhythmia therapy in response to the detection of the second arrhythmia, the second type of arrhythmia therapy having a cardiac stimulation component and a skeletal muscle component.

BRIEF DESCRIPTION OF THE DRAWINGS

The foregoing and other aspects of the present invention will be best appreciated with reference to the detailed description of the invention in conjunction with the accompanying drawings, wherein.

The drawings are not necessarily to scale.

DETAILED DESCRIPTION OF THE PREFERRED EMBODIMENT

The present invention employs a sensor to monitor cardiac electrical activity and cardiac demand in a skeletal muscle-powered cardiac assist system (hereinafter referred to as "CAS"). A basic CAS may be configured in a variety of ways as described in the aforementioned patent to Khalafalla. One specific configuration is discussed herein simply as an illustration. The present invention, however, may be used in any system concerning cardiac augmentation using skeletal muscle, such as aortic counterpulsation or a skeletal muscle ventricle. Thus it should be understood the particular configuration illustrated is not intended to limit the present invention.

The System of the Present Invention

Figure 1:
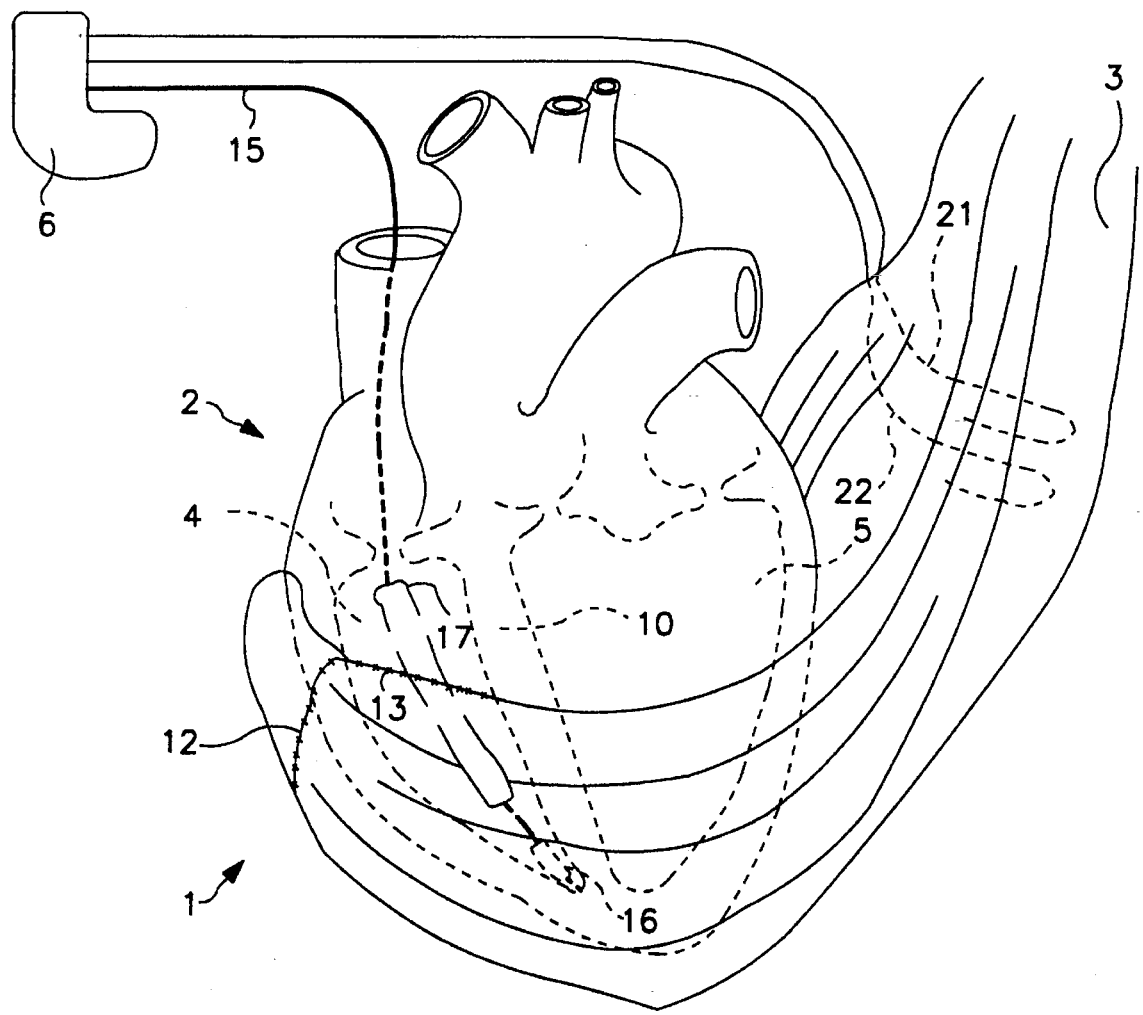
FIG. 1 illustrates an example of a system for performing both long-term stimulation of skeletal muscles for cardiac assistance using systolic augmentation as well as direct electrical stimulation of a heart according to the present invention.

FIG. 1 illustrates an example of a system 1 for performing long-term stimulation of skeletal muscles for cardiac assistance using systolic augmentation as well as direct electrical stimulation of a heart 2. As seen, skeletal muscle graft 3 is positioned about the heart 2. In the preferred embodiment the latissimus dorsi muscle is used for the skeletal muscle graft, as is well known in the art. The longitudinal fibers of the muscle graft 3 are oriented generally perpendicular to the longitudinal axes of the right ventricle 4, left ventricle 5 and interventricular septum 10 of the heart. Muscle graft 3 is positioned in this manner so that when it is stimulated, muscle graft 3 compresses ventricles 4, 5 and particularly left ventricle 5, to thereby improve the force of right and left ventricular contraction. In such a manner the overall hemodynamic output of heart 2 is increased.

In a preferred configuration, muscle graft 3 is wrapped around the heart 2 and fixedly attached to itself to form a cup-shaped "sling," using running sutures 12. Alternatively, muscle graft 3 may be attached to heart 2 using running sutures 13 as illustrated.

As seen, electrical stimulation and sensing of heart 2 is accomplished through lead 15. In particular, lead 15 electrically couples pulse generator 6 to heart 2. Lead 15 provides cardiac pacing as well as defibrillation therapies. In the preferred embodiment lead 15 is the model 6936 tripolar TRANSVENE lead from Medtronic Inc., Minneapolis, Minn. As seen, lead 15 is implanted in right ventricle 4 such that bipolar pacing electrode assembly 16 is in the right ventricular apex and defibrillation coil 17 is within the right ventricle 4. Although in the preferred embodiment a single lead is provided for pacing as well as defibrillation therapies, other types of lead configurations, such as multiple transvenous or subcutaneous or any combination thereof, may be used.

Muscle graft 3 is electrically stimulated through a pair of leads 21, 22. In particular leads 21, 22 couple pulse generator 6 to skeletal muscle graft 3. In the preferred embodiment leads 21, 22 are the model 4750 intramuscular lead from Medtronic, Inc., Minneapolis, Minn. As seen, each lead 21, 22 extends from pulse generator 6 to latissimus dorsi muscle graft 3. The electrodes (not shown) of each lead 21, 22 are placed to cause muscle graft 3 to contract when electrically stimulated, as is well known in the art. Other types of leads or electrodes, however, may be used, such as epimysial or neuromuscular leads or nerve cuff electrodes.

The Pulse Generator of the Present Invention

Figure 2:
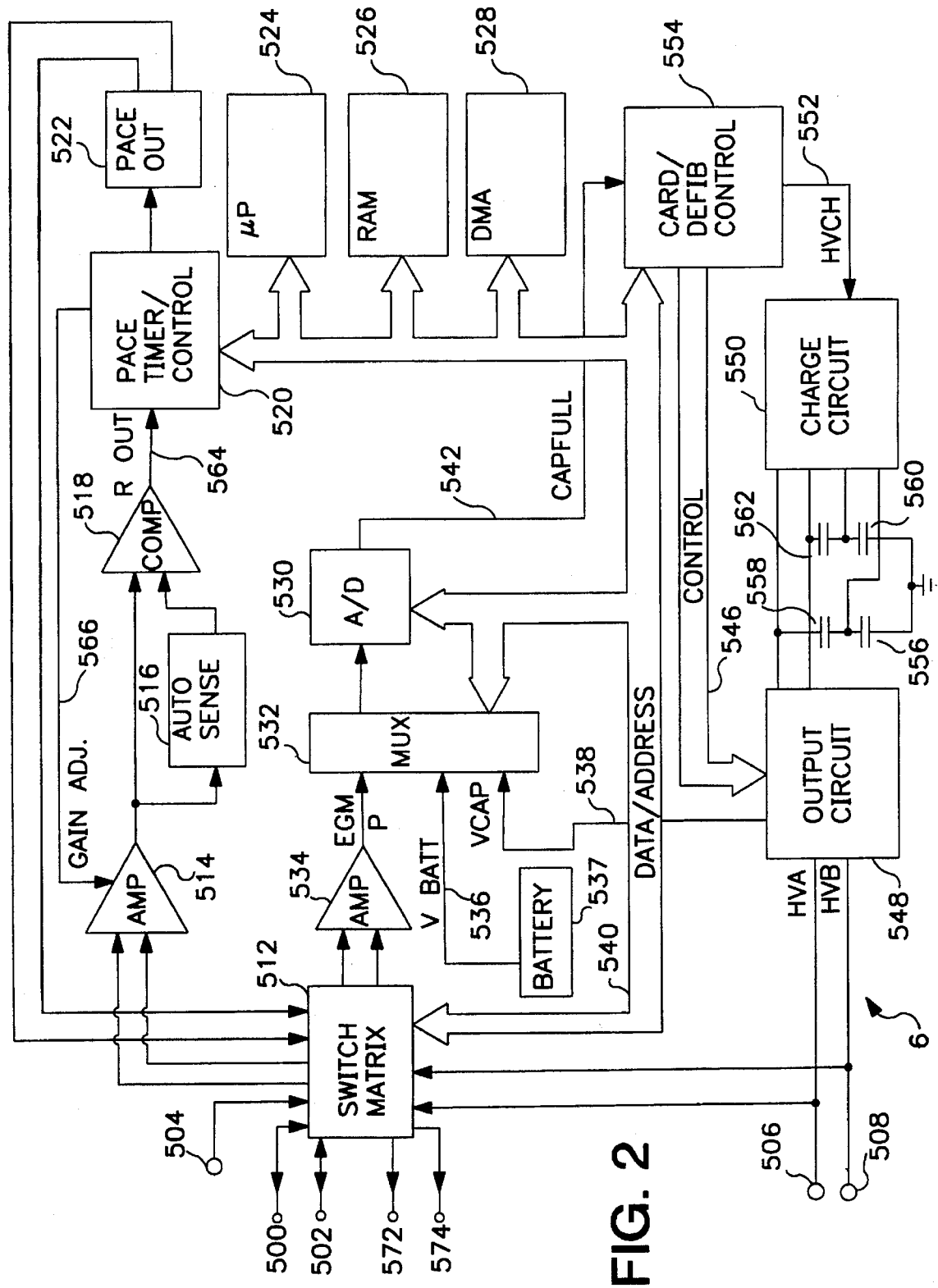
FIG. 2 is a functional schematic diagram of an implantable pulse generator used in the system of the present invention.

FIG. 2 is a functional block diagram of a pulse generator 6 in which the present invention may usefully be practiced. This diagram should only be taken, however, as exemplary of the type of device in which the invention may be embodied and not as limiting. It is believed the invention may usefully be practiced in a wide variety of device implementations. For example, the invention is also believed practicable in conjunction with the implantable muscle stimulator-pacemaker-cardioverters-defibrillators disclosed in U.S. Pat. No. 5,251,621 issued to Collins entitled "Arrhythmia Control Pacer Using Skeletal Muscle Cardiac Graft Stimulation."

The device is illustrated as being provided with six electrodes, 500, 502, 504, 506, 508, 572 and 574. Electrodes 500 and 502 may be a pair of electrodes located in the ventricle and mounted to a lead 15 as discussed above. Electrode 504 may correspond to a remote, indifferent electrode located on the housing of pulse generator 6. Electrodes 506 and 508 may correspond to large surface area defibrillation electrodes located within the right ventricle, coronary sinus, superior vena cava or may also be located subcutaneous, located on or part of the device housing or to the epicardium. Electrodes 572 and 574 are muscle stimulation electrodes coupled to the skeletal muscle wrap 3, as discussed above.

Electrodes 500 and 502 are switchable through switch matrix 512 to the R-wave detector circuit, comprising band-pass filter circuit 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by the auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned U.S. Pat. No. 5,118,824, issued to Keimel and incorporated herein by reference. However, alternative R-wave detection circuitry such as that illustrated in U.S. Pat. No. 4,819,643, issued to Menken and U.S. Pat. No. 4,880,004, issued to Baker et al., both incorporated herein by reference, may also be employed.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al., published in Biomedical Science Instrumentation, Vol. 4, pp. 67–72, 1978.

It is preferable that the threshold level not be adjusted in response to paced R-waves, but instead should continue to approach the minimum threshold level following paced R-waves to enhance sensing of low level spontaneous R-waves associated with tachyarrhythmias. The time constant of the threshold circuit is also preferably sufficiently short so that minimum sensing threshold may be reached within 1–3 seconds following adjustment of the sensing threshold equal to 70–80% of the amplitude of a detected spontaneous R-wave. The invention may also be practiced in conjunction with more traditional R-wave sensors of the type comprising a band pass amplifier and a comparator circuit to determine when the band-passed signal exceeds a predetermined, fixed sensing threshold.

Switch matrix 512 is used to select which of the available electrodes are coupled to band pass amplifier 534. Under control of microprocessor 524, switch matrix directs delivery of electrical stimulation pulses to cardiac tissue and the skeletal muscle wrap. Selection of the switch matrix settings is controlled by the microprocessor 524 via data/address bus 540. Signals from the selected electrodes are passed through band-pass amplifier 534 and into multiplexer 532, where they are convened to multi-bit digital signals by A/D converter 530, for storage in random access memory 526 under control of direct memory address circuit 528. Multiplexer 532 further receives voltage from battery 537 via VBATT 536.

Amplifier 534 may be a broad band pass amplifier, having a band pass extending for approximately 0.5 to 200 hertz. The filtered EGM signals from amplifier 534 are passed through multiplexer 532, and digitized in A-D converter circuitry 530. The digitized data may be stored in random access memory 526 under control of direct memory address circuitry 528.

The occurrence of an R-wave detect signal on line 564 is communicated to microprocessor 524 via data/address bus 540, and microprocessor 524 notes the time of its occurrence.

The remainder of the circuitry is dedicated to the provision of muscle stimulation, cardiac pacing, cardioversion and defibrillation therapies. The pacer timing/control circuitry 520 includes programmable digital counters which control the basic time intervals associated with cardiac pacing and muscle stimulation. The durations of these intervals are determined by microprocessor 524, and are communicated to the pacing circuitry 520 via address/data bus 540. Pacer timing/control circuitry also determines the amplitude of the muscle stimulation and cardiac pacing pulses and the gain of band-pass amplifier, under control of microprocessor 524.

During cardiac pacing or muscle stimulation, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502 or electrodes 572 and 574. The escape interval counter is also reset on generation of a cardiac pacing pulse, and thereby controls the basic timing of cardiac pacing functions, including anti-tachycardia pacing and subsequent muscle stimulation. The duration of the interval deemed by the escape interval timer is determined by microprocessor 524, via data/address bus 540. The value of the count present in the escape interval counter when reset by sensed R-waves may be used to measure the duration of R-R intervals, to detect the presence of tachycardia and change muscle stimulation parameters.

Microprocessor 524 operates as an interrupt driven device, and responds to interrupts from pacer timing/control circuitry 520 corresponding to the occurrence of sensed R-waves and corresponding to the generation of cardiac pacing and muscle stimulation pulses. These interrupts are provided via data/address bus 540. Any necessary mathematical calculations to be performed by microprocessor 524 and any updating of the values or intervals controlled by pacer timing/control circuitry 520 and switch matrix 512 take place following such interrupts.

In the event that a tachyarrhythmia is detected, and an antitachyarrhythmia pacing regimen is desired, appropriate timing intervals for controlling generation of anti-tachycardia pacing therapies are loaded from microprocessor 524 into the pacer timing/control circuitry 520 and switch matrix 512.

Similarly, in the event that generation of a cardioversion or defibrillation pulse is required, microprocessor 524 employs the counters in timing and control circuitry 520 to control timing of such cardioversion and defibrillation pulses, as well as timing of associated refractory periods during which sensed R-waves are ineffective to reset the timing circuitry.

Further, in the event the onset of a tachyarrhythmia is detected, but not yet confirmed, the filtered and digitized EGM available at A/D 530 will be compared by microprocessor 524 with a value from RAM 526. Measured values above set will continue detection. Values below set confirm the arrhythmia if more than 50% of the X out of Y have been detected. In the preferred embodiment X and Y are programmable counts corresponding to the VFNID and the fibrillation event buffer memory (located in the RAM 526) respectively, both of which are discussed in more detail below with regards to the VF counting mode state 34 seen in FIG. 4. Microprocessor 524 will then initiate a therapy if programmed to do so.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. During charging, microprocessor 524 enables pacer/timing control 520 to pace out 522 and switch matrix 512 to deliver muscle stimulation pulses until the high voltage capacitors 556 are sufficiently charged. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. The CAP FULL line 542 signal is sent over DATA/ADDRESS 540 to the pace timer/control 520, which then inhibits delivery of the muscle stimulation pulses.

Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in the commonly assigned U.S. Pat. No. 5,188,105 by Keimel, Method and Apparatus for Detecting and Treating a Tachyarrhythmia, incorporated herein by reference. Any known cardioversion or defibrillation pulse generation circuitry, however, is believed usable in conjunction with the present invention. For example, circuitry controlling the timing and generation of cardioversion and defibrillation pulses as disclosed in U.S. Pat. No. 4,384,585, issued to Zipes, in U.S. Pat. No. 4,949,719 issued to Pless et al., cited above, and in U.S. Pat. No. 4,375,817, issued to Engle et el., all incorporated herein by reference may also be employed. Similarly, known circuitry for controlling the timing and generation of anti-tachycardia pacing pulses as described in U.S. Pat. No. 4,577,633, issued to Berkovits et el., U.S. Pat. No. 4,880,005, issued to Pless et el., U.S. Pat. No. 7,726,380, issued to Vollmann et el. and U.S. Pat. No. 4,587,970, issued to Holley et el., all of which are incorporated herein by reference may also be used.

In modern cardiac pulse generators, the particular anti-tachycardia and defibrillation therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Prior art patents illustrating such pre-set therapy menus of antitachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current cardiac pulse generators.

In addition to varying the therapy delivered following a failed attempt to terminate a tachyarrhythmia, it is also known that adjustment of detection criteria may be appropriate. For example, adjustment may comprise reducing the number of intervals required to detect a tachyarrhythmia to allow a more rapid redetection or by changing the interval ranges to bias detection towards detection of ventricular fibrillation, for example as disclosed in U.S. Pat. No. 4,971,058, issued to Pless et al and incorporated herein by reference.

In the present invention, selection of the particular electrode configuration for delivery of the cardioversion or defibrillation pulses is controlled via output circuit 548, under control of cardioversion/defibrillation control circuitry 554 via control bus 546. Output circuit 548 switches the high voltage electrodes 506 and 508 for delivery of the defibrillation or cardioversion pulse regimen, and may also be used to specify a multi-electrode, simultaneous pulse regimen or a multi-electrode sequential pulse regimen. Monophasic or biphasic pulses may be generated. One example of circuitry which may be used to perform this function is set forth in U.S. Pat. No. 5,163,427, issued to Keimel, incorporated herein by reference. However, output control circuitry as disclosed in U.S. Pat. No. 4,953,551, issued to Mehra et al. or U.S. Pat. No. 4,800,883, issued to Winstrom both incorporated herein by reference, may also be used in the context of the present invention. Alternatively single monophasic pulse regimens employing only a single electrode pair according to any of the above cited references which disclose implantable cardioverters or defibrillators may also be used.

Operation of the System of the Present Invention

Figure 3:
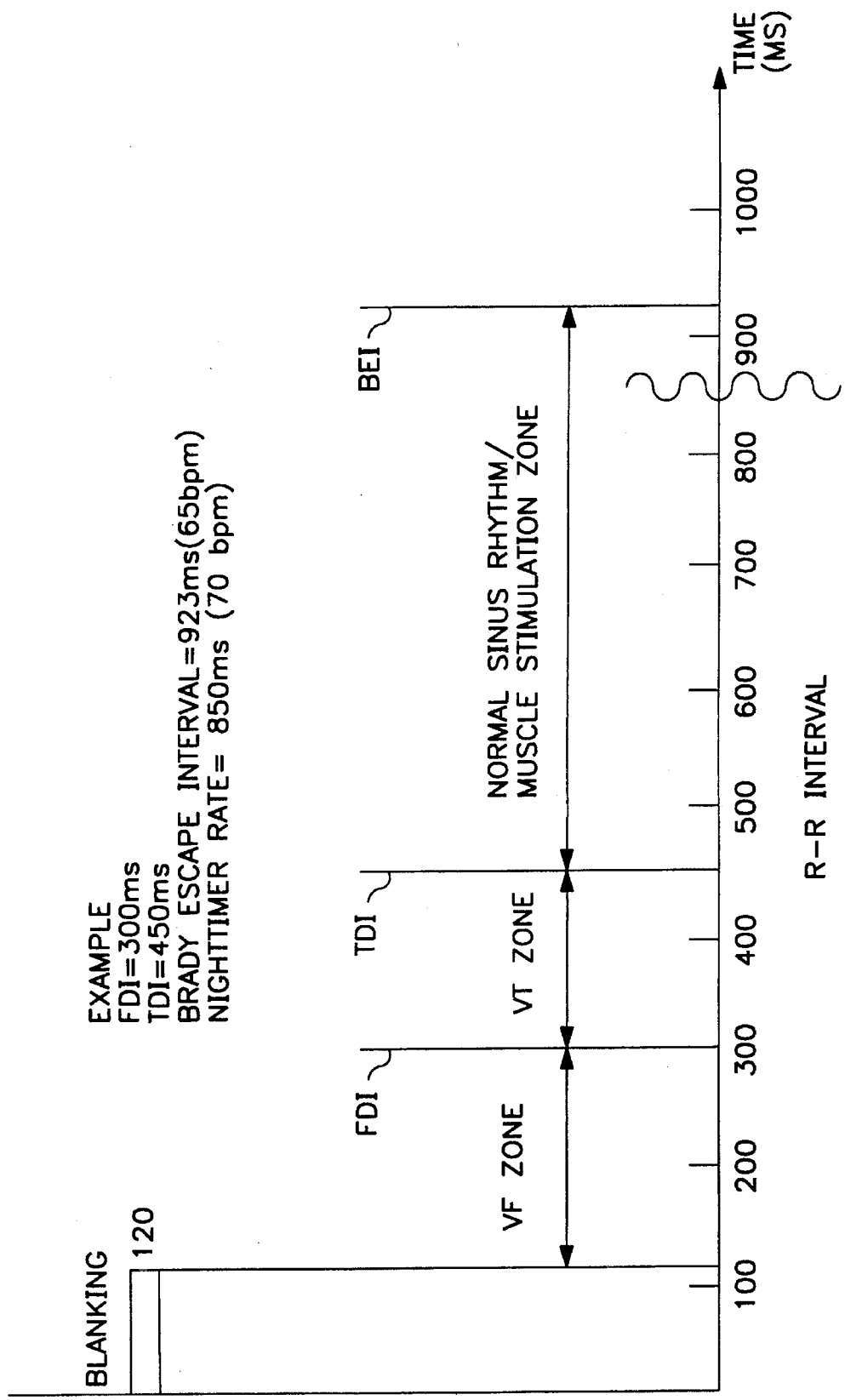
FIG. 3 is an illustration of detection interval ranges employed in a preferred embodiment of the present invention.

FIG. 3 is an illustration of detection interval ranges which may be employed in a preferred embodiment of the present invention. The specific detection interval ranges are selected and programmed by the physician. As seen, events which occur less than 120 milliseconds (hereafter "ms") apart are not detected due to blanking. This is a fixed interval and its length is not programmable by the physician. The range of intervals between detected events taken as indicative of fibrillation are greater than 120 ms and less than 300 ms. That is the fibrillation detection interval (hereafter "FDI") extends to 300 ms. This range is programmed and is selected by the physician to suit the particular patient. The range of intervals between detected events taken as indicative of tachyarrhythmia are greater than 300 ms and less than 450 ms. That is the tachyarrhythmia detection interval (hereafter "TDI") extends to 450 ms. This range is also programmed and is selected by the physician to suit the particular patient. Events having intervals between 450 ms to 923 ms, in the preferred embodiment, are taken as indicative of normal sinus rhythm. That is the brady escape interval (hereafter "BEI") extends to 923 ms. This range is also programmed and is selected by the physician to suit the particular patient. Events which occur at intervals which would be greater than the BEI are taken as indicative of bradycardia.

For example, if a first event is sensed and a second event is sensed 200 ms later, ventricular fibrillation is provisionally detected. As a second example, if a first event is sensed and second event occurs 100 ms later and a third event occurs 210 ms after the second event, then a ventricular tachycardia (hereafter "VT") is provisionally detected. This is so because the second event occurred during blanking and thus was not sensed; the third event was thereafter sensed a sum of 320 ms after the first, well within the VT zone.

It should be noted that the specific times for intervals is for the preferred embodiment and thus is only illustrative of the present invention. Other interval lengths may also be used within the scope of the present invention.

Figure 4:
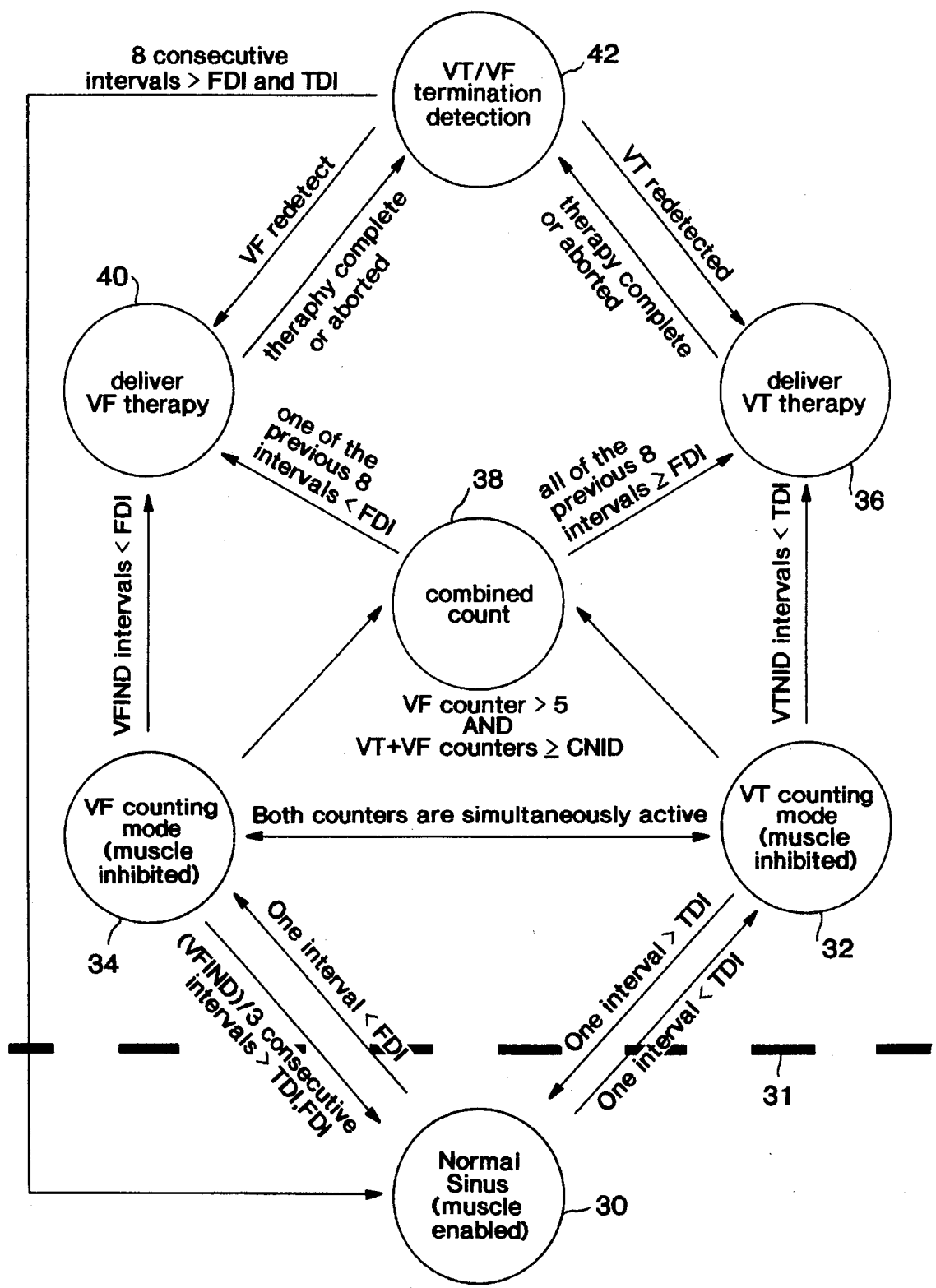
FIG. 4 is an arrhythmia detection/therapy muscle state diagram of the present invention.

FIG. 4 is an arrhythmia detection/therapy muscle state diagram of the present invention. As discussed above the present invention features skeletal muscle graft stimulation as well as cardiac stimulation. One of the important requirements of such a system, however, is to accurately detect cardiac arrhythmias and respond with the appropriate therapy. As discussed above, concurrent skeletal muscle graft stimulation may interfere with the detection and diagnosis of arrhythmias. Thus, one important feature of the present invention is the manner in which it provides for skeletal muscle graft stimulation as well as cardiac stimulation while also managing the prompt detection and diagnosis of arrhythmias. In particular, the present invention temporarily stops or inhibits skeletal muscle stimulation once the onset of an arrhythmia is sensed.

As seen, during normal sinus rhythm the system remains at normal sinus rhythm state 30. In state 30 device provides both skeletal muscle graft stimulation and any bradycardia stimulation required. Bradycardia stimulation may take the form of any suitable electrical stimulation therapy, and preferably is given in the form of VVI pacing, although other types of pacing therapy may be delivered, such as VOO, OVO and VVT. Bradycardia stimulation is delivered, in the preferred embodiment, upon the detection of a sequence of cardiac events in which the range of intervals between detected events greater than BEI.

If, however, a sequence of cardiac events is detected in which the range of intervals between detected events is less than the TDI, then the skeletal muscle stimulation is inhibited (as represented by line 31) and VT counting mode state 32 is reached. In the preferred embodiment, if only one TDI is detected, then the skeletal muscle stimulation is inhibited and VT counting mode state 32 is reached.

While in the VT counting mode state 32, the skeletal muscle stimulation is re-enabled and the device returns to normal sinus rhythm state 30 if one interval greater than the TDI is detected.

In addition, when a sequence of cardiac events is detected in which the range of intervals between detected events is less than the FDI, then the skeletal muscle stimulation is inhibited (as represented by line 31) and VF counting mode state 34 is reached. In the preferred embodiment, if only one FDI is detected, then the skeletal muscle stimulation is inhibited and VF counting mode state 34 is reached.

While in the VF counting mode state 34, if VT detection is programmed on, the skeletal muscle stimulation is re-enabled and the device returns to normal sinus rhythm state 30 upon the detection of consecutive events with intervals greater than TDI equal to one-third of the number of intervals to detect VF (hereafter "VFNID"). If, however, VT detection is programmed off, the skeletal muscle stimulation is re-enabled and the device returns to normal sinus rhythm state 30 upon the detection of consecutive intervals greater than FDI equal to one-third of VFNID. Of course, if VT detection is programmed off, deliver VT therapy state 36 may still be reached through combined count state 38, discussed below.

It should be noted because FDI is smaller than TDI, then when VF counting mode state 34 is reached, this necessarily implies VT counting mode state 32 is also reached. From an electronic circuit design perspective, however, the counting bins for each state are simultaneously active, although both not necessarily registering events at the exact same time.

While in VT counting mode state 32 the device counts the number of events which meets the TDI criterion. When the cumulative VT event counter is equal to the number of intervals to detect VT, also called VTNID, then VT detection is fulfilled, deliver VT therapy state 36 is reached and VT therapy is delivered. In the preferred embodiment VTNID is programmable. As discussed in more detail below, VT detection and deliver VT therapy state 36 may also be reached through combined count state 38.

While in the VF counting mode state 34 the device counts the number of events which meet the FDI criterion. When the cumulative event counter is equal to VFNID, then VF detection is fulfilled, deliver VF therapy state 40 is reached and VF therapy is delivered. In the preferred embodiment VFNID is programmable. As discussed above, VFNID essentially is the number of past events that must satisfy the FDI criteria to be detected as fibrillation. The count uses past events that have been stored in the fibrillation event buffer memory (located in the RAM 526 of FIG. 2) which include both paced and sensed events. For example, if VFNID is set to 18 and fibrillation event buffer is set to 24; then to detect VF 18 of the last 24 events must satisfy the FDI criteria. As seen, deliver VF therapy state 40 may also be reached combined count state 38.

Combined count state 38 is provided to avoid excessive detection times during competing VT and VF counters. Thus combined count state 38 is reached, in the preferred embodiment, when the VF event counter reaches five and the VT event counter plus the VF event counter is greater than or equal to the combined number of intervals to detect parameter (hereafter "CNID"). In the preferred embodiment CNID is not directly programmable, but rather is equal to seven sixths of VFNID. Once the combined count state 38 is reached, then the second look criterion is applied.

Second look criterion is used only after combined count state 38 is reached. Second look criterion is applied to determine whether VT or VF therapy should be delivered. In the preferred embodiment second look criterion is as follows: If all of the previous 8 intervals are greater than or equal to FDI, then the VT detected path should be followed and deliver VT therapy state 36 is reached, but if one of the previous 8 intervals is less than FDI, then the VF detected path will be followed and deliver VF therapy state 40 is reached.

Once deliver VF therapy state 40 is reached, VF therapy is completed or aborted and VT/VF termination detection state 42 is reached. Similarly once deliver VT therapy state 36 is reached, VT therapy is completed or aborted and VT/VF termination detection state 42 is reached.

While in VT/VF termination detection state 42, the device determines whether VT or VF is re-detected. If either VT or VF is detected, then the device returns to the relevant therapy state. If neither VT nor VF is re-detected, the device returns to normal sinus state 30. VT/VF termination detection is accomplished as follows: If VT detection is programmed "Off" and eight consecutive events having intervals greater than FDI are sensed, then VF termination is detected and the device returns to normal sinus state 30. If VT detection is programmed "On" and eight consecutive events having intervals greater than TDI (which by definition is greater than FDI) are sensed, then VT termination is detected and the device returns to normal sinus state 30.

As discussed above the present invention also features skeletal muscle stimulation while charging for defibrillation. Essentially this feature provides muscle stimulation pulses to the grafted skeletal muscle while the device is charging a capacitor to deliver a defibrillation pulse. As mentioned above, because the muscle continues to contract and causes cardiac perfusion to be maintained. This cardiac perfusion, in turn, limits the increase in the overall defibrillation threshold. Because the increase in these thresholds is minimized, this permits the device to feature smaller capacitors or lower voltages or both.

Figure 5:
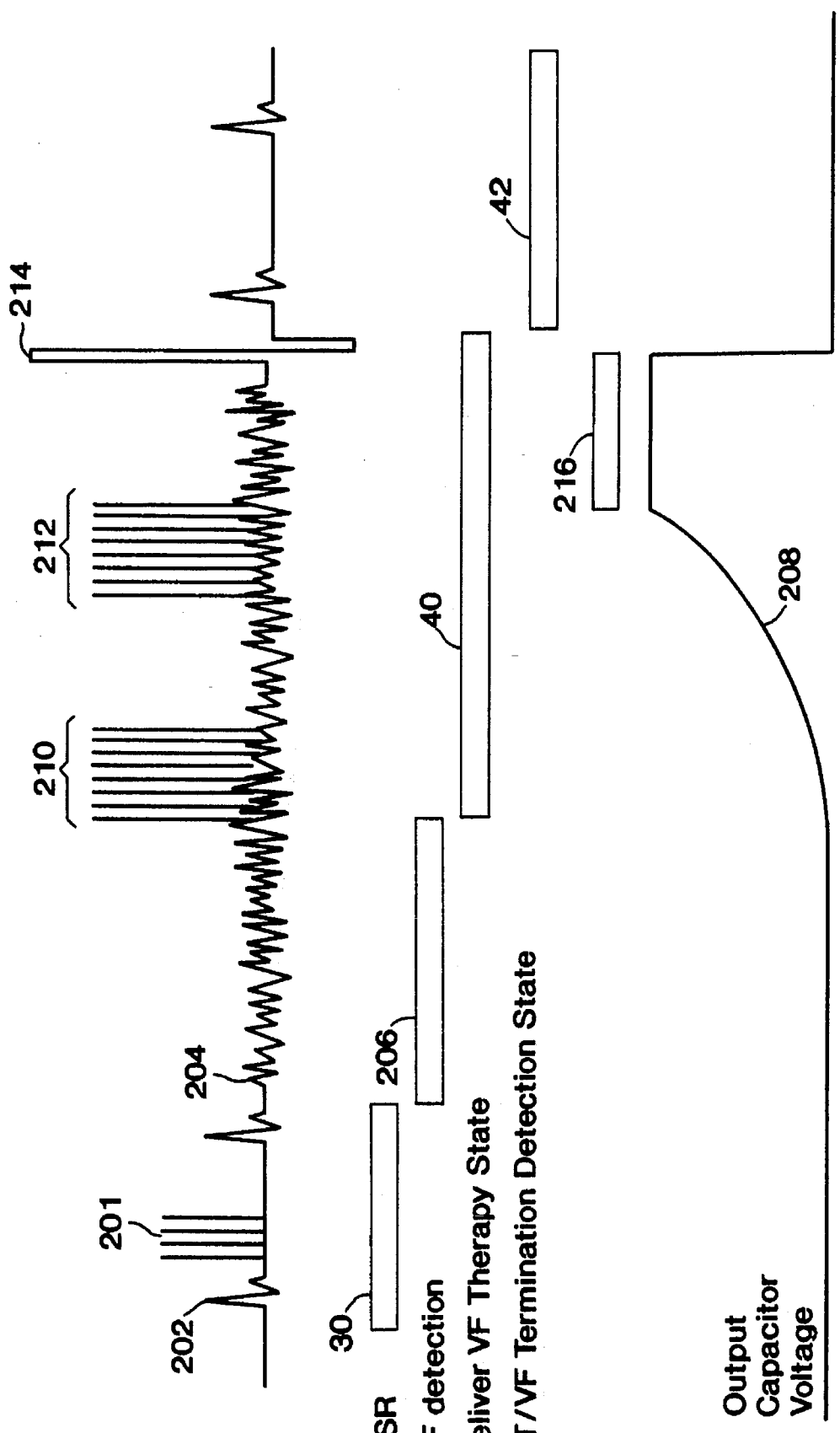
FIG. 5 is a timing diagram showing the relationship between muscle stimulation, cardiac events, and a defibrillation charge cycle.

FIG. 5 is a timing diagram showing the relationship between muscle stimulation, cardiac events and a defibrillation charge cycle. As seen, during normal sinus rhythm, represented here by normal QRS complex 202 the device is in normal sinus state 30. As such, muscle stimulation burst 201 is delivered to stimulate the skeletal muscle graft and thereby provide cardiac assistance, as described above. At first occurrence of a VF event 204 device enters detection state 206. As explained in FIG. 4, during detection state 206 device is in VF counting mode state 34 and VT counting mode state 32. As also explained in FIG. 4 once a VF event 204 is detected all muscle stimulation is inhibited, as may be seen in the lack of any muscle bursts in the region of detection state 206. Once VF is confirmed the device then enters deliver VF therapy state 40.

While in deliver VF therapy state 40, device performs several operations, including charging of the output capacitors, depicted as line 208. In addition, skeletal muscle stimulation is re-initiated and a series of asynchronous muscle stimulation bursts 210, 212 are delivered. In the preferred embodiment asynchronous bursts 210, 212 have a greater amplitude than muscle stimulation burst 201, on the order of one and a half times as large.

Once charging of the output capacitors is completed, a sequence to synchronize the defibrillation discharge to a sensed R-wave is undertaken. In particular, device begins a synchronization sequence during synchronization time 216. Synchronization sequence is undertaken to synchronize defibrillation discharge to a sensed cardiac event as well as to re-confirm the presence of the arrhythmia. If the synchronization sequence is successful, then defibrillation discharge 214 is delivered synchronized to a sensed cardiac event. If the synchronization sequence is unsuccessful, then defibrillation discharge 214 is delivered at the timing out of synchronization time 216. In addition during synchronization time 216, device re-inhibits skeletal muscle stimulation in order to permit reliable sensing of any intrinsic cardiac events.

Figure 6:
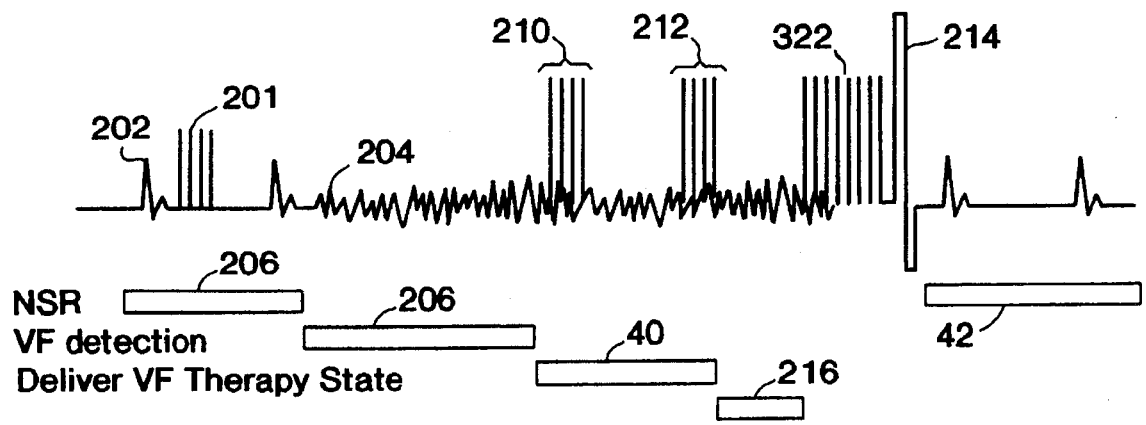
FIG. 6 is a timing diagram showing the relationship between muscle stimulation and cardiac events of an alternate embodiment.

FIG. 6 is a timing diagram showing the relationship between muscle stimulation and cardiac events of an alternate embodiment. In particular, in an alternate embodiment, if synchronization is unsuccessful, then the device delivers an asynchronous muscle stimulation burst 322 immediately prior to defibrillation discharge 214, as best seen in FIG. 6. Muscle stimulation burst 322 is intended to cause the heart to be squeezed by the skeletal muscle graft and achieve roughly a systolic position when defibrillation discharge 214 is delivered. Because the volume of the heart in such a position is decreased the defibrillation threshold is likewise decreased.

Turning again to FIG. 5, once defibrillation discharge 214 is delivered, then device enters into VT/VF termination detection state 42 to thereby confirm heart has returned to normal sinus rhythm.

Figure 7:
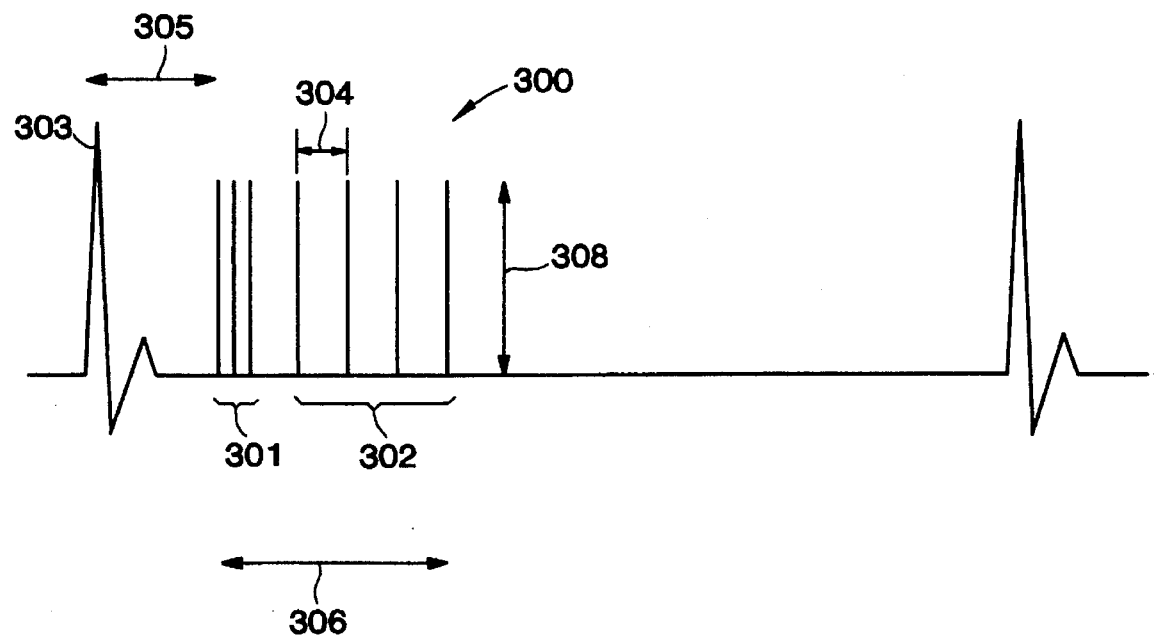
FIG. 7 depicts an alternate muscle stimulation burst which may be used with the present system.

FIG. 7 depicts an alternate muscle stimulation burst which may be used with the present system. These muscle stimulation bursts may be used at any suitable time within the present system, and are not limited to only use prior to delivery of the defibrillation therapy. As seen muscle stimulation burst 300 occurs after QRS 303 in the amount of a synchronization delay 305. In the preferred embodiment synchronization delay 305 is programmable and is undertaken in order to synchronize the muscle stimulation burst 300 with the ventricular contraction. Muscle stimulation burst 300 has essentially two sections, first section 301 and second section 302, often referred to as "muscle catch" and "muscle pulse train" respectively. As seen, first section 301 has a smaller interpulse interval 304 within the burst, i.e. a higher frequency. In comparison second section 302 has a relatively larger interpulse interval 304 within the burst, i.e. a relatively smaller frequency. The higher frequency first section 301 increases the velocity and force of the skeletal muscle graft contraction. In the preferred embodiment interpulse interval 304 and number of pulses in the catch may be selected by the physician. The pulse waveform, amplitude 308 and width of the muscle catch are the same for the remainder of the burst.

Figure 8:
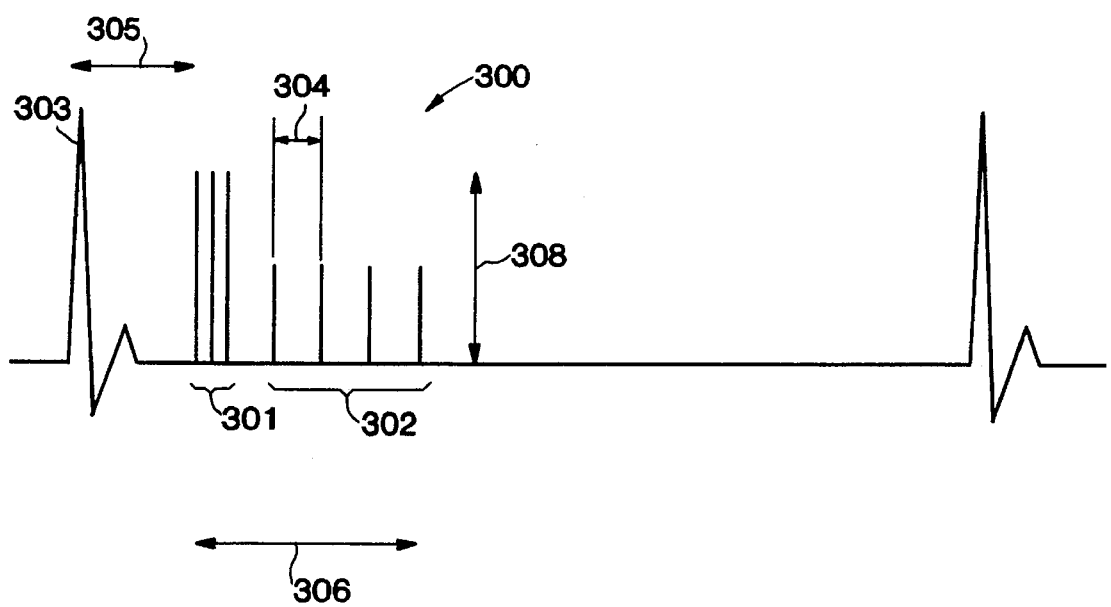
FIG. 8 depicts an alternate embodiment of the muscle catch stimulation which may be used with the present system.

FIG. 8 depicts an alternate embodiment of the muscle catch stimulation which may be used with the present system. As seen all parameters of the muscle stimulation burst 300 are the same as that described above with respect to FIG. 7 but for the amplitude of second section 302.

Figure 9:
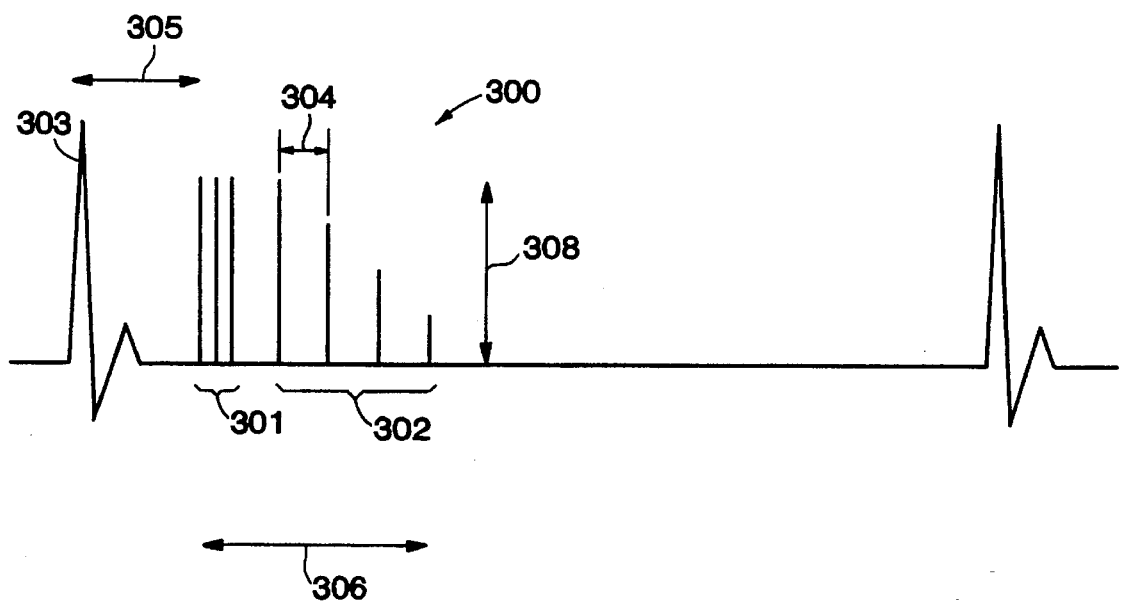
FIG. 9 depicts an alternate embodiment of the muscle catch stimulation which may be used with the present system.

FIG. 9 depicts an alternate embodiment of the muscle catch stimulation which may be used with the present system. As seen all parameters of the muscle stimulation burst 300 are the same as that described above with respect to FIG. 7 but for the amplitude of second section 302. In particular amplitude of each burst within second section 302 decreases. The rate of decrease of pulse amplitude within each burst decreases as a function of rate, i.e. the faster the rate of muscle stimulation, the greater the decrease of pulse amplitude within the pulse train.

As discussed above, the mechanically induced cardiac output augmentation of the present invention during VF (which is associated with loss of cardiac output) leads to maintaining defibrillation thresholds during prolonged episodes of fibrillation, thus resulting in longer battery life or smaller device size or both. It also permits a longer charging interval without the concern of a dangerously low or temporarily lost cardiac output.

While the present invention has been described in detail with particular reference to a preferred embodiment, it will be understood variations and modifications can be effected within the scope of the following claims. Such modifications may include substituting elements or components which perform substantially the same function in substantially the same way to achieve substantially the same result for those described herein.

What is claimed is:

1. An apparatus for stimulating a skeletal muscle grafted about a heart, detecting cardiac events and delivering therapeutic stimulation to the heart comprising:

means for delivering stimulation to a skeletal muscle grafted about a heart;

means for sensing depolarizations of a patient's heart;

means for measuring the intervals separating successive depolarizations of the patient's heart;

means for defining first and second interval ranges;

means for determining the number of the measured intervals falling within the first and second interval ranges;

means for inhibiting the means for delivering stimulation to a skeletal muscle grafted about a heart upon the sensing of a depolarization within the first or second interval range;

first means for detecting the occurrence of a first type of arrhythmia when the number of the measured intervals falling within the first interval range equals a first predetermined value;

second means for detecting the occurrence of a second type of an arrhythmia when the number of the intervals falling within the second interval range equals a second predetermined value;

means for delivering to the patient's heart a first type of arrhythmia therapy in response to the detection of the first arrhythmia by the first detecting means; and means for delivering to the patient's heart and to the skeletal muscle grafted about the heart a second type of arrhythmia therapy in response to the detection of the second arrhythmia by the second detecting means, the second type of arrhythmia therapy having a cardiac stimulation component and a skeletal muscle component.

2. An apparatus according to claim 1 wherein the means for delivering first and second intervals comprise means for defining first and second intervals which are adjacent and non-overlapping.

3. An apparatus according to claim 1 wherein the means for delivering the second type of arrhythmia therapy comprises means for delivering a defibrillation pulse and means for delivering a defibrillation stimulation to the skeletal muscle grafted about the heart.

4. An apparatus according to claim 1 wherein the means for delivering a first type of arrhythmia therapy comprises means for delivering antitachycardia pacing pulses.

5. An apparatus according to claim 1 further comprising means for defining a third interval range, the third interval range encompassing intervals larger than the first interval range.

6. An apparatus according to claim 1 further comprising means for detecting a third type of arrhythmia and means for initiating a third type of arrhythmia therapy in response to the detection of the third type of arrhythmia.

7. An apparatus according to claim 6 wherein the third type of arrhythmia therapy comprises bradycardia pacing pulses.

8. An apparatus according to claim 1 wherein the means for delivering the second type of arrhythmia therapy further comprises:

means for temporarily storing energy;

means for charging the means for temporarily storing energy;

means for re-initiating delivering stimulation to a skeletal muscle grafted about a heart during the charging of the means for temporarily storing energy.

* * * * *